United States Patent [19]

Sullivan

[11] Patent Number: 4,604,206

[45] Date of Patent: Aug. 5, 1986

[54] STAGED ANAEROBIC REACTOR

[75] Inventor: Richard A. Sullivan, Brookfield, Wis.

[73] Assignee: Envirex Inc., Waukesha, Wis.

[21] Appl. No.: 782,823

[22] Filed: Oct. 2, 1985

Related U.S. Application Data

[62] Division of Ser. No. 546,800, Oct. 31, 1983, Pat. No. 4,568,457.

[51] Int. Cl.$^4$ ............................................... C02F 3/28
[52] U.S. Cl. ................................. 210/603; 210/612; 210/619; 210/218; 48/197 A; 435/167
[58] Field of Search ............... 210/603, 619, 612, 613, 210/150, 151, 180, 195.1, 256, 261, 262, 218; 435/167, 316, 300; 48/111, 197 A

[56] References Cited

U.S. PATENT DOCUMENTS

| | | | |
|---|---|---|---|
| 2,315,577 | 4/1943 | Bach | 210/613 |
| 4,022,665 | 5/1977 | Ghosh et al. | 210/603 |
| 4,067,801 | 1/1978 | Ishida et al. | 210/603 |
| 4,211,647 | 7/1980 | Friedman et al. | 210/150 |
| 4,248,972 | 2/1981 | Fischer et al. | 210/180 |
| 4,429,043 | 1/1984 | Paton | 210/603 |

FOREIGN PATENT DOCUMENTS 0078919 5/1983 European Pat. Off. ............ 210/612

*Primary Examiner*—Benoît Castel
*Attorney, Agent, or Firm*—Lawrence J. Crain

[57] ABSTRACT

An industrial waste anaerobic digestion process takes place in a digester having separate sections within the digester, in which the acid forming and gas forming phases of the digestion process can occur separately under conditions optimized for each phase. A rotating biological contactor is provided in each section for increasing the liquid/gas interface to facilitate the anaerobic reaction. A series of partitions is provided in each section to create zones in which the waste concentration is extremely high and on which the biota can react at maximal reaction rates. The $CO_2$ produced in the acid forming phase is used in both acid and gas forming sections to mix and achieve pH adjustment, and the methane can be used in the gas forming sections for mixing. A thermophilic chamber in the center of the tank is surrounded by the mesophyllic chamber to minimize and utilize conductive heat loss.

10 Claims, 3 Drawing Figures

STAGED ANAEROBIC REACTOR

This application is a division of application Ser. No. 546,800, filed 10/31/83, now U.S. Pat. No. 4,568,457.

BACKGROUND OF THE INVENTION

This invention relates to anaerobic reactors and more particularly to the staged reactor in which the mesophyllic and thermophilic biota in both acid forming and gas forming phases are segregated into separate sections, and each section is divided into several stages in which rotating biological contactors are employed with carbon dioxide by-product recirculation from the acid forming phase of both mesophyllic and thermophilic sections for the purpose of optimizing reaction kinetics and the quality and quantity of methane gas production.

The use of anaerobic digestion for municipal and industrial waste product reduction and stabilization of the removed waste products has been widely practiced in the past, primarily because of the degree of sludge reduction and the potential for production of usable methane gas. Although these reactors were well accepted by both industrial and municipal waste disposal authorities, they are not being utilized in nearly as many applications for which they are suited primarily because of certain practical and financial considerations regarding their construction and use.

The standard practice at present is to employ a large cylindrical tank in which all anaerobic reactions occur. The gas output from the anaerobic reactor is typically a mixture of carbon dioxide and methane gas of relatively low commercial value. The produced gas is used primarily to mix the contents of the reactor by injection in lances or in a bubble gun, and the excess gas is burned in a gas burner which maintains the temperature of the liquid in the tank to the required temperature for thermophilic, more commonly, mesophyllic reaction, whichever is used in that reactor.

In industrial waste disposal plants employing waste of a biological oxygen demand much higher than that seen in municipal plants, typically higher than 1,000 parts per million BOD, the burden on the municipal plant is extreme. In these applications, the potential gas production and sludge reduction is much greater in anaerobic reactors than in aerobic reactors, so the use of anaerobic reactors in industrial applications becomes potentially extremely attractive. However, the potential has never been achieved in any available apparatus and therefore the usual practice is for the industry to simply pay heavy user fees to municipal plants where the high strength waste is mixed with ordinary municipal waste and treated in the usual municipal waste water treatment plant. This represents a waste of potentially valuable resources and also constitutes an unnecessary expense to the industry and burden on the municipal plant.

Anaerobic digesters are not sufficiently utilized by industry because the initial investment for design and installation for such a system is high, the land area required for the typical large anaerobic digestion tank is large, the energy output is insufficient and of low quality and the sludge production is excessive and of insufficient purity for safe disposal. The result of these factors is that the installation and maintenance costs extend the payback period so far into the future that the purchase of such a system becomes economically unattractive.

Thus, the industry has long been in need of an anaerobic digester that is designed to achieve high energy yield and low volumes of high purity sludge, and does so in an apparatus that is small in land use area and both mechanically and biologically reliable.

SUMMARY OF THE INVENTION

Accordingly, it is an object of this invention to provide an anaerobic reactor which is capable of producing high purity methane gas from high strength industrial waste. Another object of the invention is to provide an anaerobic reactor having small volume and small land use requirements but capable of treating a large volumetric flow rate of industrial waste. Yet another object of the invention is to provide an anaerobic reactor which is biologically and mechanically reliable and has low maintenance costs while producing a commercially valuable by-product, so that the payback period is sufficiently short to make its installation an economically attractive proposition to the industry.

These and other objects of the invention are achieved in the preferred embodiment of the invention in which the acid forming and gas forming phases of the digestion process are separated into separate vessels within the digester. Within each section, a rotating biological contactor is provided which increases the liquid/gas interface to increase the anaerobic reaction. In each section, a series of partitions is provided to provide zones of extremely high waste concentration on which the biota can react at maximal reaction rates. The $CO_2$ produced in the acid forming phase is used in both acid and gas forming sections to provide mixing and achieve pH adjustment. A thermophilic chamber in the center of the tank is surrounded by the mesophyllic chamber to minimize and utilize conductive heat loss.

DESCRIPTION OF THE DRAWINGS

The invention and its many attendant objects and advantages will become better understood by reference to the following detailed description of the preferred embodiment when read in conjunction with the following drawings, of which.

DESCRIPTION OF THE PREFERRED EMBODIMENT

Figure 1:
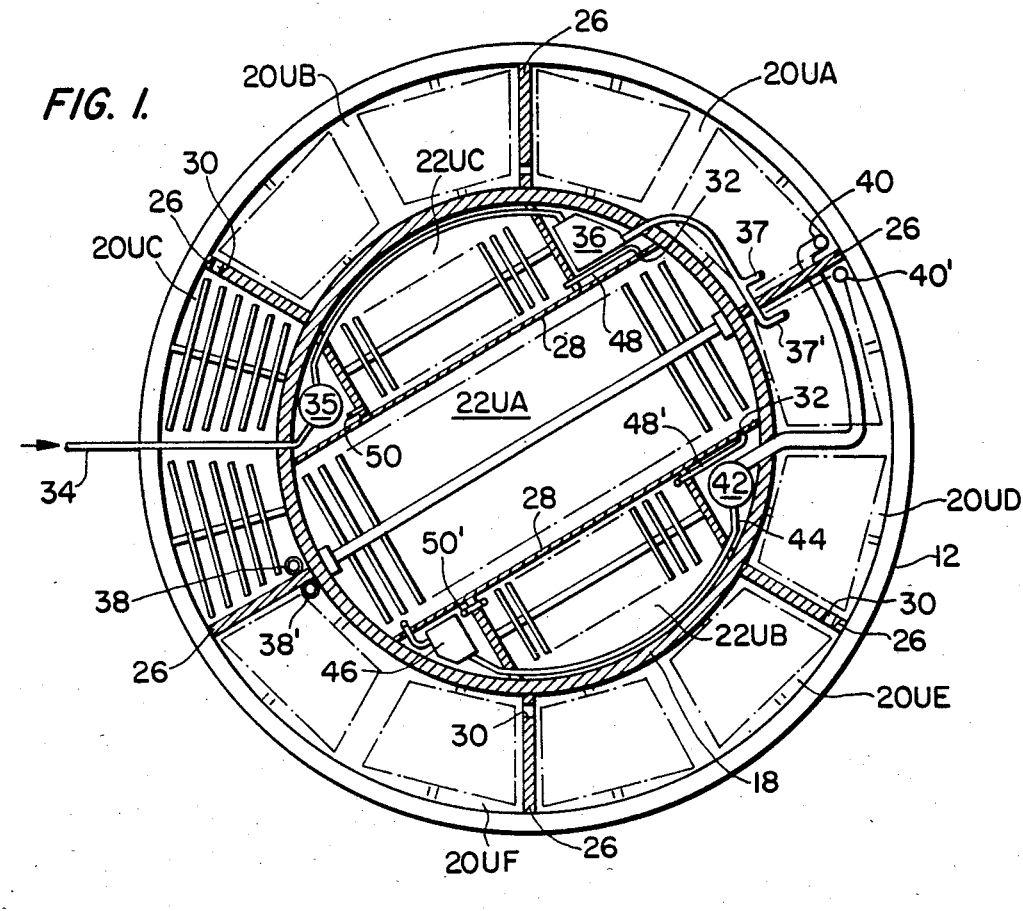
FIG. 1 is a sectional plan view of a top section of an anaerobic reactor according to this invention.
Figure 2:
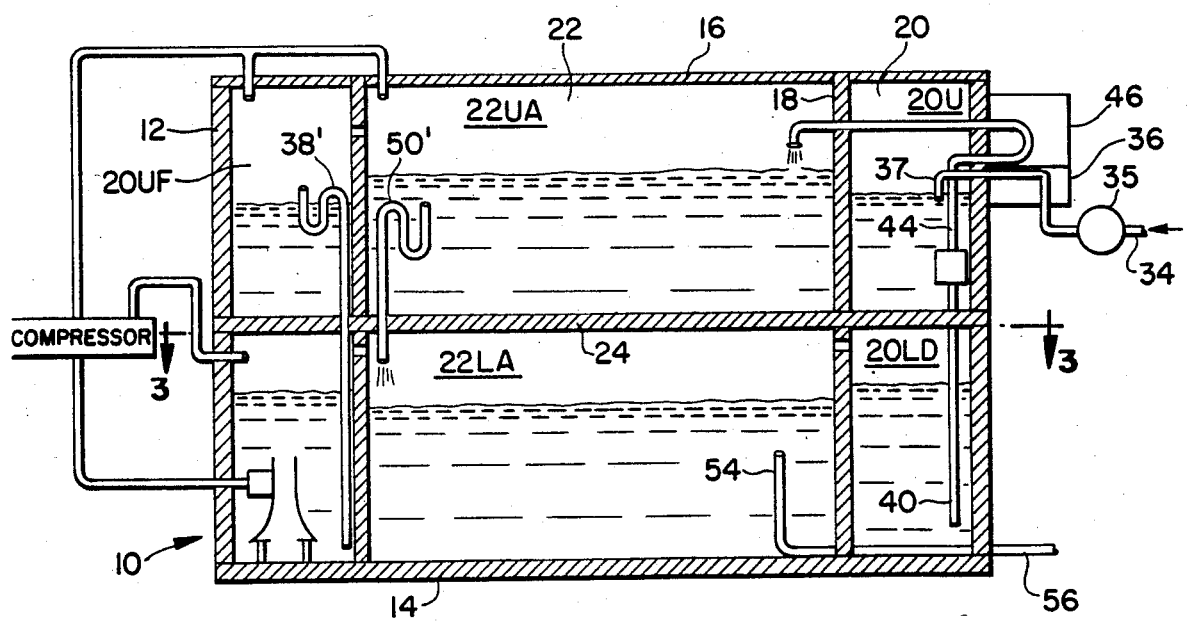
FIG. 2 is a sectional elevation of the reactor shown in FIG. 1.
Figure 3:
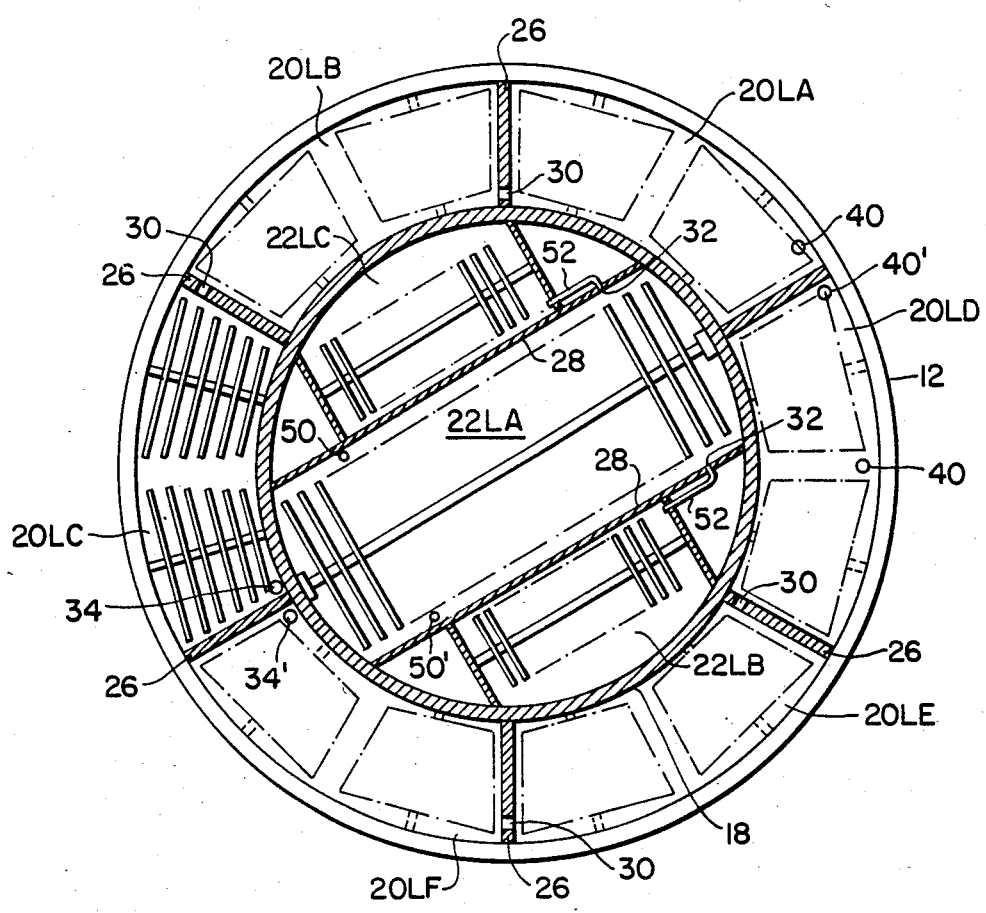
FIG. 3 is a plan view along lines 3—3 of the lower section of the reactor shown in FIG. 2.

Referring now to the drawings wherein like reference characters identify identical or corresponding parts, and more particularly to FIGS. 1-3 thereof, a cylindrical tank 10 is shown having an upright cylindrical wall 12, a circular bottom plate 14, and a cover 16. The cover 16 may be a fixed or a floating cover as shown in U.S. Pat. No. 2,050,915, incorporated herein by reference. As shown most clearly in FIG. 1, a cylindrical wall 18 is disposed concentrically within the outer wall 12 and is fixed in place by welding to the bottom plate 14 or by other suitable means. The cylindrical wall 18 divides the tank into an anular chamber 20 and an inner cylindrical chamber 22. A horizontal partition 24 may be provided at about the mid height position in the tank to separate the chambers 20 and 22 into upper and lower sections 20U, 20L, 22U and 22L. Each of the upper and lower annular chambers 20U and 20L may be divided by radial partitions 26 into sectors 20UA through 20UF and 20LA through 20LF. Likewise, the cylindrical inner chamber 22 may be divided by secant partitions 28 into segments 22UA through C and 22LA through C.

In each of the several chambers, section, sectors and segments (hereinafter referred to collectively as "compartments"), the wastewater is treated by biological organisms, called "biota," which are effective for the particular environment that exists in that particular compartment. The biota will typically be different in each compartment. The biota in each compartment grows on a fixed media structure, described in detail below, so it does not move from one compartment to the next with the flow of wastewater, but rather stays fixed in its own compartment.

A liquid flow control system is provided to achieve a controlled flow of liquid to be treated from the input through the various compartments in which they are treated by the different forms of biota to achieve maximum reduction and stabilization of impurities in the water. Each of the partitions 26 and 28 is provided with openings 30 and 32 respectively for the purpose of allowing a controlled flow of liquid from one sector or segment to the next. The liquid flow control system includes a metered inlet pipe 34 from a liquid heater 36 in which the waste water is raised to the desired temperature for optimum biological activity by the biota in the upper annular chamber sectors 20UA through 20UC. Simultaneously, liquid is introduced through a second inlet pipe 34' after being heated in the heater 36 to the same temperature and is introduced into upper annular chamber sector 20UF from whence it flows through chambers 20UE and 20UD for staged biological treatment as explained more fully hereinafter.

A pair of gravity feed tubes 38 and 38' are provided in the upper annular chamber sectors 20UA and 20UD to enable liquid in those chambers above a certain level to flow into lower annular chamber sectors 20LA and 20LD, respectively. In those chamber sectors, the liquid flows in the opposite direction from chamber sectors 20LA through 20LC, and from chamber sectors 20LD through 20LF. In its passage through these chamber sectors, the liquid is treated by different forms of biota than the biota in the upper chamber sectors, as is discussed further below.

A liquid outlet 40 in chamber 20LD and a liquid outlet 40' in chamber 20LF is connected to a pump 42 which pumps the liquid from the lower annular chamber sectors 22LD and 22LE through a line 44 to a supplemental heater 46. The heater 46 raises the temperature of the liquid to the temperature which is optimum for the biological activity in the inner cylindrical chamber 22. The liquid flows through the center segment 22UA of the upper cylindrical inner chamber 22U, and exits at the far end through liquid lines 48 and 48' into the adjacent segments 22UC and 22UB, respectively, of the upper cylindrical inner chamber 22U. The liquid flows in parallel through these two chambers and exits at the far end of each through gravity feed tubes 50 and 50' whence it flows into the central segment 22LA of the lower section 22L of the cylindrical inner chamber 22. The liquid flows through the lower cylindrical chamber segment 22LA and then passes out the remote end of that segment through two feed lines 52 and 52' and into the adjacent end of the two adjacent segments 22LB and 22LC. The liquid flows in parallel through these last mentioned segments to a pair of drains 54 which are connected to a fluid outlet 56.

The liquid flow control system, described above, for controlling the flow of liquid through the several sections and sectors of the inner and outer chambers enables a single anaerobic digestion tank to be converted or constructed initially in such a way as to provide for isolation of the different biota operating in the system and for staging of the digestion in each separate section. The apparatus also optimizes the thermodynamics of the entire system by utilizing one hundred percent of the heat lost from the thermophilic section and reducing to a minimum the surface area through which heat from the low temperature is lost.

This arrangement of four different treatment sections, each broken into separate sections and sectors, makes it possible to provide thermophilic and mesophyllic sections for both acid forming and gas forming digestion phases. In this way, it is possible to produce the optimum conditions for these various treatments of the waste water in separate sections to achieve the maximum possible effect with the smallest possible equipment size and cost. In addition, by staging the treatment in the several sections and sectors of the upper and lower chambers, it is possible to obtain the benefit of extremely high biological activity in the first stage in which the waste water contamination is at the highest concentration and then continue the treatment in lower concentration sectors and segments to achieve an overall purity over the entire range of activity of the biota in the several sections well in excess of anything possible in presently available treatment apparatus.

Specifically, in the treatment apparatus shown in FIGS. 1 and 2 the waste water is first introduced through the inlet 34 and pumped through the pump 35 through a heater 36 and is introduced through ports 37 and 37' into the mesophyllic acid forming phase sectors 20UA and 20UD. In these sectors and in the other phased sectors of the mesophyllic acid forming phase section the waste water is treated by biota which breaks down the complex organic waste materials into simple organic acids, aldehydes and alcohols. The by-product of this conversion is carbon dioxide gas which is collected and utilized in a manner to be disclosed below.

The liquid outflow from the mesophyllic acid forming phase chambers, containing some residual complex organic matter and the organic acids, aldehydes and alcohols formed by the acid forming biota formed in the upper annular chamber sectors, flows into the lower annular chamber sectors 20LC and 20LF where it is subjected to biological treatment by the separate biota in those chambers which metabolize the organic acids, aldehydes and alcohols to produce methane gas and water. The pH of the liquid for optimum metabolic rate of the biota in the gas forming phase is lower than that in the acid forming phase and must be adjusted to the correct range in order to obtain the optimal results. In addition to pH adjustment, it is necessary for the liquid in the tank to remain sufficiently mixed so that any solids that are produced or any bacteria cell bodies that come loose from the media on which they are held remain in suspension and pass through the entire system without building up any solid layer on any sector or segment. These two purposes namely pH control and mixing, are accomplished by introducing $CO_2$ gas produced in the acid forming phase through conventional mixers in the segments and sectors. These mixers are of various types well known in the art such as bubble gun mixers, gas injections lances, submerged turbines and other known forms of mixers.

In the event that the pH of this solution reaches the lower end of the optimum range and further injection of $CO_2$ into solution would carry it below that range, the pH can be adjusted by injection of a buffering agent or other pH adjusting chemical. It is not desirable to introduce a different gas into the gas forming phase for mixing because it would not be absorbed into the liquid and would dilute the methane gas formed in the gas forming phase. One important advantage of this system is the purity of methane gas produced and the use of another gas such as nitrogen would reduce that purity. Naturally, gas scrubbers could be used to reduce such dilution, but I prefer to prevent the dilution in the first place rather than remove it once it has occurred. It may be possible to utilize the methane gas itself as a mixing gas, provided large bubble mixing is used which would reduce the retarding effect that I believe methane produces on the biota in the system.

One advantage of using a rotating biological contactor in the device is that it enormously increases the gas liquid interface and facilitates the removal of methane from the external cell wall of the biota. I believe that speedy removal of the methane molecules from the external cell wall increases the metabolic rate of the bacteria such that reaction rates much higher than that possible in anaerobic systems, even those laboratory systems which optimize the conditions for the particular biota involved, may be obtained.

After treatment in the mesophyllic sections 20U and 20L, the waste water is pumped through the pump 42 and supplemental heater 46 into the upper cylindrical inner chamber where it is treated with a thermophilic acid forming bacteria whose preferential substrate has a molecular size greater than that for the mesophyllic bacteria, and therefore metabolizes a slightly different range of materials than the mesophyllic bacteria. In this way, a wider range of waste materials can be treated under optimum materials, resulting in a much greater reduction of the waste products, at greater through-put rates, with the smaller equipment size and cost.

The liquid output from the thermophilic acid forming phase is introduced into the thermophilic gas forming phase where it is treated by the particular biota which operate in that range. As in the mesophyllic gas forming phase, the carbon dioxide produced in the acid forming phase is utilized for pH adjustment and mixing. Likewise, acidic adjustment may be made by the appropriate injection of the adjusting chemicals.

The output from the side sections of the thermophilic gas forming phase flow through a drain 54 and through an outlet 56 for reuse as plant water, for draining to local bodies of water or, if other untreated waste products are present, to the municipal waste water treatment plant.

Depending on analysis of the waste liquid stream, it may be necessary to add nutrients for the optimal growth and metabolism of the neutralizing biota. For example, the waste stream may contain insufficient nitrogen, phosphorus, aluminum or calcium and other trace elements may be necessary to provide the optimal nutritional environment of the bacteria, and these must be added, preferably in liquid form, to the segments and sectors in which they are found to be insufficient, to produce optimum metabolic rates. This process is preferably accomplished automatically by sensors in the tank which signal a control circuit to operate a liquid feed pump to maintain the concentration of the various nutritional constituents within the optimal range. It may also be desirable to provide chemical precipitators in liquid form to precipitate these or other constituents when they exceed the optimal range. In this way it is possible to maintain the ideal environment to achieve the maximum possible benefit of the biota in the various sectors and segments.

The biota in the system is held in a fixed media matrix within each of the several sectors and segments so that the biota which is most effective for treating the particular form and concentration of waste in that particular sector or segment is preferentially developed on the media. The preferred form of fixed media is the rotating biological contactor disclosed in U.S. Pat. No. 3,837,559 issued Aug. 6, 1974 to Gass and Prosser. The device disclosed in the U.S. Pat. No. 3,837,559, is particularly suitable for this application because of the enormous surface area of the contactor and because the biota grows in a thin layer over this enormous surface area to provide a fixed media reactor, which prevents circulation of the biota from chamber to chamber, in a surface area that exceeds many other conventional forms of fixed media system. In addition, this system, by utilizing a submerged ratio of between 70 and 40 percent enables the liquid-to-gas interface to be optimized for the particular biota involved so that the reaction kinetics and the methane off-gassing can be optimized in each chamber separately.

The rotation of the rotating biological contactors is preferably by means of an air drive system such as that disclosed and claimed in U.S. Pat. No. 3,886,074 issued on May 27, 1975 to Prosser. The driving gasses in this application would be the methane and $CO_2$ gasses in the various chambers. In this way, the $CO_2$ gas is used for three purposes: (1) pH adjustment, (2) mixing in the tank, (3) utilization as a precursor in the biological reaction that produces methane, and (4) use as an energy vehicle to rotate the rotating biological contactor.

The cover 16 and the horizontal partition 24 make it possible to pressurize the gas over both the acid and the methane forming phases of the system. The degree of pressurization may differ for the various biota involved and can be selected by a brief period of experimentation with the particular waste and biota generated for treatment of that waste. I have found that pressurization is often effective although the exact reasons are a matter of theory. My theory is that the higher pressure in the methane forming phase promotes dissolving of the $CO_2$ in the liquid where it is effective to lower pH; in the methane gas formation chambers, the high pressure is less effective in maintaining the methane gas in solution because methane is hydrophobic and therefore the turbulence and large liquid/gas interface promotes the off gassing of the hydrophobic methane despite the higher pressure. A higher pressure in the methane forming chambers than in the acid forming chambers will tend to support a partition 24 so that a lower strength material may be used safely.

The disclosed invention provides for isolation of the media packs for the purpose of isolating the attached biology. In this way, the biota employed in acid formation will be isolated from the biota employed in gas production, and the acid formation and gas production phases will be sequential and isolated, and each phase can be optimized through manipulation of environmental conditions for the purpose of optimizing both reaction kinetics and the quality of gas produced. Moreover, the media packs may be staged in both acid and gas formation phases such that the biochemical and the chemical reaction kinetics of high order may be obtained by achieving high concentrations in the upstream segments. The elevated pressure of the gas layer above the liquid level, and the gas liquid interface on the great surface area of the rotating biological contactors makes it possible for the dissolved $CO_2$ concentration in the liquid to be maintained at a higher than normal rate and the methane off-gassing to be facilitated by virtue of the periodic draining of the liquid from the biota and the turbulence of that liquid layer. The system also provides for optimal utilization of the $CO_2$ gas produced in the acid phase including liquid mixing, methane precursor, pH adjustment, and rotating biological contactor drive energy transference. The system enables the degree of submergence of the rotating biological contactor to be optimized for each of the several chambers and also permits optimizing of the rotational speed of the contactor to suit the conditions in each chamber. This is done simply by positioning the gas outlet in the chamber with respect to the air cups on the air drive and, when the $CO_2$ concentration in the liquid must be limited, by increasing the bubble size or by decreasing the bubble size and diverting the $CO_2$ injection to regions in the chamber involved where it does not produce a driving effect on the RBC.

Obviously, numerous modifications and variations of the disclosed embodiment will occur to those skilled in the art in view of this disclosure. Therefore it is expressly to be understood that these modifications and variations and the equivalents thereof may be practiced without departing from the spirit and scope of the invention as defined in the following claims.

What is claimed is:

1. A method of anaerobically digesting organic substances in wastewater, comprising:
    establishing an acid forming microorganism colony on a first large surface area RBC in a first closed chamber;
    establishing and maintaining the temperature, pH, and nutrient conditions for at least 80% of the growth rates of said acid forming microbes in said first closed member;
    submerging and rotating said RBC in said wastewater at a rotational speed and a level between 10–90% submerged, selected for optimal gas/liquid and liquid/biota contact, to obtain the optimal $CO_2$ solution and liquid turbulence at the biota cell wall, and rotating said RBC about its axis;
    isolating and compressing the off-gasses produced by said acid forming microbes, and utilizing at least a portion of said compressed off gasses to mix said wastewater and to adjust the pH of said wastewater by a controlled supply of said off-gasses to locations submerged in said wastewater;
    establishing a methane forming microorganism on a second large surface RBC in a second closed chamber in liquid communication with said first closed chamber;
    establishing and maintaining the optimum temperature, pH, and nutrient conditions for maximal growth rates of said methane forming microorganism in said second chamber;
    submerging and rotating said second RBC in said wastewater at a rotational speed and a level between 10–90% submerged, selected to approach optimal gas/liquid and liquid/biota contact to obtain the optimal methane off-gassing and liquid turbulence at the biota cell wall;
    isolating, collecting, and compressing the methane gas produced by said methane forming microbes for commercial or industrial utilization.

2. A method of anaerobically digesting organic substances out of wastewater and in so doing producing a commercially useful methane gas, comprising the steps of:
    providing a vessel having an inlet, at least four separate compartments, and an outlet;
    establishing a population of a respectively different digesting microorganism in each of the compartments, at least one of the microorganisms being of a type which produces a methane gas;
    flowing the wastewater through the compartments of the vessel according to a predetermined sequence;
    controlling the temperature and acidity of the wastewater respectively within each of the separate compartments to optimize the environment for the biological activity in that compartment, including using $CO_2$ gas evolved in one compartment to control the pH level in another, whereby the organic substances in the wastewater are effectively digested by the different microorganisms and a methane gas of commercially acceptable purity is formed; and
    isolating, collecting and removing said methane gas.

3. The method of claim 2, further including the steps of establishing and acid forming mesophyllic bacteria in one of the compartments and a methane producing mesophyllic bacteria in another of the compartments.

4. The method of claim 3, further including the steps of establishing an acid forming thermophilic bacteria in one of the compartments and a methane producing thermophilic bacteria in another of the compartments.

5. The method of claim 4, further including the step of establishing any one or more of said bacteria on a fixed media form situated in the compartment containing that bacteria.

6. The method of claim 5, wherein said fixed media form comprises a rotating biological contactor unit situated in each of said compartments.

7. A method of anaerobically treating wastewater and in so doing producing a commercially useful methane gas, comprising the steps of:
    providing a supply of wastewater;
    providing a vessel having an inlet, an outlet, and at least four distinct compartmentalized treatment phases comprised of thermophilic acid forming, thermophilic gas forming, mesophyllic acid forming and mesophyllic gas forming phases;
    providing a population of phase-specific biota in each of said phases;
    creating an optimum nutritive and temperature environment in each of said populations of biota in each of said compartments;
    heating said flow of wastewater prior to its introduction into the first compartment;
    pumping said wastewater into said mesophyllic acid forming phase wherein said resident population of acid forming biota breaks down said wastewater into simple organic acids, aldehydes and alcohols, and evolving carbon dioxide gas;
    collecting said evolved carbon dioxide gas;
    passing the liquid outflow from said mesophyllic acid forming phase into said mesophyllic gas forming phase, wherein said resident population of gas forming biota breaks down said organic acids, aldehydes and alcohol into methane gas and water;

adjusting the pH in said gas forming phase to maintain optimum growth conditions for said biota;

mixing the waste liquid in said gas forming phase to prevent settling of suspended solid matter;

reheating said flow of wastewater from said mesophyllic phase;

passing said flow of wastewater from said mesophyllic gas forming phase to said thermophilic acid forming phase for further digestion of organic materials by said resident biota;

collecting carbon dioxide gas evolved from said thermophilic gas forming phase;

introducing wastewater output from said thermophilic acid forming phase to said thermophilic gas forming phase, where it is treated by resident gas-forming biota;

collecting evolved methane gas from said thermophilic gas forming phase;

draining the liquid output from said thermophilic gas forming phase into a local body of water or for further treatment in a municipal treatment plant; and providing a rotating biological contactor unit in each of said treatment compartments.

8. The method of claim 7, wherein the carbon dioxide gas which is collected in said acid forming phases is used to adjust the pH in said gas forming phases.

9. The method defined in claim 7, wherein said methane gas forming phases are pressurized.

10. The method defined in claim 9, wherein said methane gas forming phases are maintained at a higher pressure than said acid forming phases.

* * * * *